United States Patent
Wang et al.

(10) Patent No.: US 11,020,447 B2
(45) Date of Patent: *Jun. 1, 2021

(54) COMPOSITIONS, KITS AND METHODS FOR TREATING TYPE II DIABETES MELLITUS

(71) Applicant: VITNOVO, INC., Taipei (TW)

(72) Inventors: Pei-Ran Wang, Taipei (TW); Rey-Yuh Wu, Taipei (TW); Yu-Yuan Wu, Taipei (TW); Lung-Yu Kuan, Taipei (TW); Klim King, Taipei (TW)

(73) Assignee: VITNOVO, INC., Taipei (TW)

( * ) Notice: Subject to any disclaimer, the term of this patent is extended or adjusted under 35 U.S.C. 154(b) by 238 days.

This patent is subject to a terminal disclaimer.

(21) Appl. No.: 15/844,696

(22) Filed: Dec. 18, 2017

(65) Prior Publication Data

US 2018/0140653 A1   May 24, 2018

Related U.S. Application Data

(63) Continuation-in-part of application No. 15/359,555, filed on Nov. 22, 2016.

(51) Int. Cl.
| | |
|---|---|
| *A61K 36/906* | (2006.01) |
| *A61P 3/10* | (2006.01) |
| *A61K 45/06* | (2006.01) |
| *A61K 38/28* | (2006.01) |
| *A61K 38/26* | (2006.01) |
| *A61K 31/4985* | (2006.01) |
| *A61K 31/7048* | (2006.01) |
| *A61K 31/155* | (2006.01) |

(52) U.S. Cl.
CPC .......... *A61K 36/906* (2013.01); *A61K 31/155* (2013.01); *A61K 31/4985* (2013.01); *A61K 31/7048* (2013.01); *A61K 38/26* (2013.01); *A61K 38/28* (2013.01); *A61K 45/06* (2013.01); *A61P 3/10* (2018.01); *A61K 2236/50* (2013.01); *A61K 2300/00* (2013.01)

(58) Field of Classification Search
None
See application file for complete search history.

(56) References Cited

U.S. PATENT DOCUMENTS

| | | | | |
|---|---|---|---|---|
| 2007/0275907 A1* | 11/2007 | Chen | .................... | C07D 311/96 514/23 |
| 2011/0195139 A1* | 8/2011 | Wu | ..................... | A61K 36/906 424/756 |

* cited by examiner

*Primary Examiner* — Terry A McKelvey
*Assistant Examiner* — Catheryne Chen (57) ABSTRACT

Disclosed herein are methods for treating type II diabetes mellitus. In particular, the present invention relates to methods of using an extract of *Hedychium coronarium* Koenig and a blood glucose reduction agent, to synergistically reduce the blood glucose level of the subject having type II diabetes mellitus.

10 Claims, 2 Drawing Sheets

COMPOSITIONS, KITS AND METHODS FOR TREATING TYPE II DIABETES MELLITUS

CROSS-REFERENCE TO RELATED APPLICATION

This application is a continuation-in-part of U.S. Ser. No. 15/359,555 filed Nov. 22, 2016, which is a continuation application of U.S. Ser. No. 13/015,256 filed Jan. 27, 2011, now abandon, which claims priority to U.S. Ser. No. 12/701,997 filed Feb. 8, 2010; the disclosure of afore-indicated prior applications are incorporated herein by reference in their entireties.

BACKGROUND OF THE INVENTION

1. Field of the Invention

The present disclosure is generally directed to methods of treating hyperglycemia, particularly, type II diabetes mellitus.

2. Description of Related Art

Type II diabetes or non-insulin-dependent diabetes mellitus (NIDDM) has been found to possess inheritable aspects which can be greatly impacted by external environmental factors. The underlying etiologies of type II diabetes include deficiencies in insulin-producing beta cells; altered response to insulin by muscle, adipose, and liver cells; and abnormalities in the regulating mechanisms responsible for controlling carbohydrate and lipid metabolism following ingestion of food. Modulation in insulin-sensitivity is affected by environmental factors and behaviors, mostly a sedentary lifestyle and obesity. The cellular mechanisms that contribute to modulation of muscle and adipose cell sensitivity to insulin are complex and are not well understood. It is believed that altering insulin signaling pathways, increasing the amount of intracellular fat, and elevating levels of free fatty acids and other adipose tissue products can impact insulin-sensitivity.

If not properly controlled or stabilized, a hyperglycemic state would inevitably result in comorbidities including cardiovascular disease, vision impairment, various forms of neuropathy and cognitive impairment, stroke, and peripheral vascular disease. The common therapeutic approach, in addition to major modifications in an individual's dietary nutrition and physical activity, includes the use of anti-hyperglycemic drugs and insulin. Since the disease is chronic and progressive, and so far no treatment is able to reverse the progression, and thus there remains in this field a need of an improved methods and/or medicaments for treating type II diabetes.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present invention relates to a medicament, which alone or in combination with any blood glucose reduction agent, do effectively reduce the blood glucose level of a hyperglycemia subject, particularly, a subject having type II diabetes mellitus.

Accordingly, one aspect of the present disclosure relates to a method of treating a subject having type II diabetes. The method comprises administering to the subject an effective amount of a plant extract of *Hedychium coronarium* Koenig and a blood glucose reduction agent, in which the combined treatment results in a synergistically reduction in the blood glucose level in the subject, thereby alleviating and/or ameliorating symptoms related to type II diabetes.

According to embodiments of the present disclosure, the plant extract of *Hedychium coronarium* Koenig suitable for use in the present method is produced by a method comprising:

(a) extracting an overground part of *Hedychium coronarium* Koenig with a solvent to obtain a first extract, wherein the solvent is (1) petroleum ether, (2) n-hexane, (3) dichloromethane, (4) trichloromethane, (5) ethyl acetate, (6) acetone, or (7) ethanol at a concentration of 70-100% (v/v in water), or (8) a combination of any of (1) to (7), (b) loading the first extract onto a first ion exchange chromatography column, (c) washing the first ion exchange chromatography column with a solution of water and ethanol at a volume ratio from 1:1 to 1:9, and (d) eluting the first ion exchange chromatography column with ethanol at a concentration of at least 70% (v/v in water) to produce the plant extract.

Figure 1A:
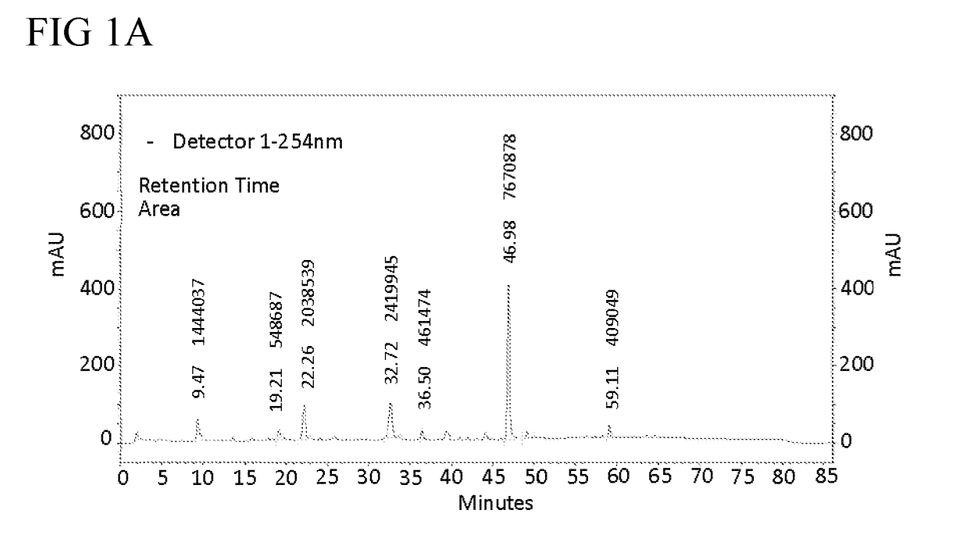
FIG. 1A is the HPLC spectrums of the HC extract prepared in accordance with Example 1.1 of this invention.

According to one embodiment of the present disclosure, the plant extract of *Hedychium coronarium* Koenig prepared by the afore-mentioned method has a HPLC spectrum substantially as illustrated in FIG. 1A.

Figure 1B:
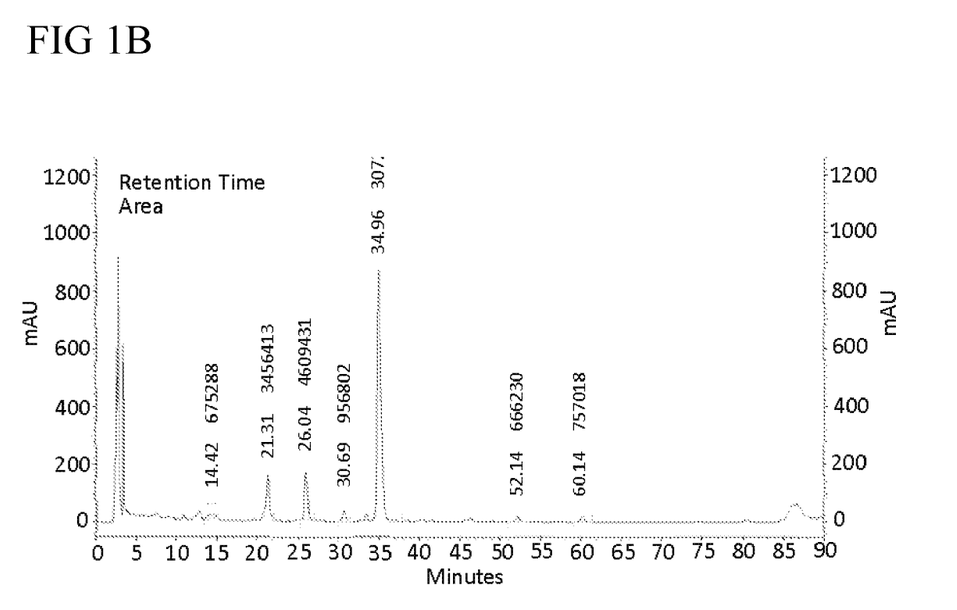
FIG. 1B is the HPLC spectrums of the HC extract prepared in accordance with Example 1.2 of this invention.

According to another embodiment of the present disclosure, the plant extract of *Hedychium coronarium* Koenig prepared by the afore-mentioned method has a HPLC spectrum substantially as illustrated in FIG. 1B.

According to embodiments of the present disclosure, the blood glucose reduction agent may be selected from the group consisting of, dipeptidyl peptidase-4 (DPP-4) inhibitor, insulin, an insulin analogue, biguanide, sulfonylurea, thiazolidinedione (TZD), sodium-glucose co-transporter 2 (SGLT2) inhibitor, α-glycosidase inhibitor, glucagon-like peptide 1 (GLP-1) receptor agonist, and a combination thereof.

According to embodiments of the present disclosure, the DPP-4 inhibitor is gliptins. Suitable examples of gliptins include, but are not limited to, sitagliptin, vildagliptin, saxagliptin, linagliptin, gemigliptin, anagliptin, teneligliptin, alogliptin, trelagliptin, dutogliptin, omarigliptin, berberine, and lupeol.

According to one preferred embodiment of the present disclosure, the method comprises administering to the subject an effective amount of the plant extract of *Hedychium coronarium* Koenig and the DDP-4 inhibitor. Preferably, the DDP-4 inhibitor is sitagliptin.

According to embodiments of the present disclosure, the insulin analogue is glargine, degludec or detemir.

According to embodiments of the present disclosure, the biguanide is metformin, phenformin, or bufomin. According to another preferred embodiment of the present disclosure, the method comprises administering to the subject an effective amount of the plant extract of *Hedychium coronarium* Koenig and the biguanide. Preferably, the biguanide is metformin.

According to embodiments of the present disclosure, the sulfonylurea is glibenclamide, gliclazide, glimepiride, or glipizide.

According to embodiments of the present disclosure, the TZD is pioglitazone, rosiglitazone, lobeglitazone, ciglitazone, darglitazone, englitazone, netoglitazone, rivoglitazone, or troglitazone.

According to embodiments of the present disclosure, the SGLT2 inhibitor is dapagliflozin, empagliflozin, canagliflozin, Ipragliflozin, tofogliflozin, sergliflozin etabonate, remogliflozin etabonat, or ertugliflozin.

According to embodiments of the present disclosure, the α-glycosidase inhibitor is acarbose, miglitose, or voglibose.

According to embodiments of the present disclosure, the GLP-1 receptor agonist is liraglutide, exenatide, albiglutide or LY2189265.

According to some preferred embodiments of the present disclosure, the present method comprises administered to the subject the plant extract of *Hedychium coronarium* Koenig and a combination of biguanide and DDP-4 inhibitor. Preferably, the biguanide is metformin, and the DDP-4 inhibitor is sitagliptin.

According to preferred embodiments of the present disclosure, the plant extract of *Hedychium coronarium* Koenig and the blood glucose reduction agent are independently administered orally, intravenously, intramuscularly, subcutaneously, transmucosally, or intrarectally to the subject. In one preferred embodiment, the plant extract of *Hedychium coronarium* Koenig and the blood glucose reduction agent are both administered orally. Accordingly, the plant extract of *Hedychium coronarium* Koenig and the blood glucose reduction agent suitable for oral administration may be provided as tablets, pills, granules, powders, solutions, suspensions, syrups or capsules.

According to embodiments of the present disclosure, the plant extract of *Hedychium coronarium* Koenig and the blood glucose reduction agent are respectively administered in the amount of about 0.1 to 100 mg/Kg. Preferably, the plant extract of *Hedychium coronarium* Koenig and the blood glucose reduction agent are respectively administered in the amount of about 1 to 20 mg/Kg.

Many of the attendant features and advantages of the present disclosure will becomes better understood with reference to the following detailed description considered in connection with the accompanying drawings.

BRIEF DESCRIPTION OF THE DRAWINGS

The present description will be better understood from the following detailed description read in light of the accompanying drawings, where.

DESCRIPTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the specification, examples and appended claims are collected here. Unless defined otherwise, all technical and scientific terms used herein have the same meaning as commonly understood by one of the ordinary skill in the art to which this invention belongs.

The singular forms "a", "and", and "the" are used herein to include plural referents unless the context clearly dictates otherwise. The term "about" as used herein generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, or reflection angles disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

"*Hedychium coronarium* Koenig" as used herein is an herbaceous perennial monocot plant (Family: Zingiberaceae, Order: Zingiberales, Genus: *Hedychium*). The plant is native to India, Malaysia and Himalaya Mountains, and generally grows at lower elevations. In Taiwan, it can be found in mountain areas, fields, and gullies of Yilan, Taipei, Hsinchu, Taichung and Kaohsiung. The underground part includes rhizomes, which look like a ginger; and the overground part includes leaves and pseudostems formed by the leaf sheaths. The leaves are lance-shaped, 40 cm in long and 7 cm in wide, and smooth in the up sides and hairy in the down sides. Lips and petals are white and fragrant. *Hedychium coronarium* Koening reaches about 1-2 m in height and grows tufts, and makes great potted plants and cut flowers. The tender shoots and rhizomes are eatable. *Hedychium coronarium* Koening is also named as butterfly ginger, butterfly lily, ginger lily, ginger orchid, white butterfly lily, Gandasuli, and Kamia.

The term "treatment" as used herein are intended to mean obtaining a desired pharmacological and/or physiologic effect, e.g., reducing blood glucose level in a hyperglycemia subject. The effect may be prophylactic in terms of completely or partially preventing a disease or symptom thereof and/or therapeutic in terms of a partial or complete cure for a disease and/or adverse effect attributable to the disease. "Treatment" as used herein includes, but is not limited to, preventative (e.g., prophylactic), curative or palliative treatment of a disease in a mammal, particularly human; and includes: (1) preventative (e.g., prophylactic), curative or palliative treatment of a disease or condition (e.g., diabetes mellitus or disorders related thereto) from occurring in an individual who may be pre-disposed to the disease but has not yet been diagnosed as having it; (2) inhibiting a disease (e.g., by promoting the proliferation of insulin-producing beta cells or suppressing apoptosis of these cells); or (3) relieving a disease (e.g., reducing symptoms associated with the disease).

The term "administered", "administering" or "administration" are used interchangeably herein to refer a mode of delivery, including, without limitation, orally, intravenously, intramuscularly, intraperitoneally, intraarterially, intracranially, transmucosally (e.g., inhalation, and intranasally), or subcutaneously administering of an agent (e.g., a compound or a composition) of the present invention. In preferred embodiments, the plant extract of *Hedychium coronarium* Koening of the present disclosure is formulated into compositions that are suitable for oral administration.

The term "an effective amount" as used herein refers to an amount effective, at dosages, and for periods of time necessary, to achieve the desired result with respect to the treatment of a disease resulted from hyperglycemia. For example, in the treatment of diabetes mellitus, an agent (i.e., the present compound) which decrease, prevents, delays or suppresses or arrests any symptoms related to diabetes mellitus would be effective. An effective amount of an agent is not required to cure a disease or condition but will provide a treatment for a disease or condition such that the onset of the disease or condition is delayed, hindered or prevented, or the disease or condition symptoms are ameliorated. The specific effective or sufficient amount will vary with such factors as the particular condition being treated, the physical condition of the patient (e.g., the patient's body mass, age, or gender), the type of mammal or animal being treated, the duration of the treatment, the nature of concurrent therapy (if any), and the specific formulations employed and the like. Effective amount may be expressed, for example, as the total mass of the active agent (e.g., in grams, milligrams or micrograms) per day, or as the weight of the active agent per Kg of the body weight. The effective amount may be divided into one, two or more doses in a suitable form to be administered at one, two or more times throughout a designated time period. Further, persons having ordinary skills could calculate the human equivalent dose (HED) for the medicament (such as the compounds of the present disclosure) based on the doses determined from animal models set forth in the working examples of the present disclosure. For example, one may follow the guidance for industry published by US Food and Drug Administration (FDA) entitled "Estimating the Maximum Safe Starting Dose in Initial Clinical Trials for Therapeutics in Adult Healthy Volunteers" in estimating a maximum safe dosage for use in human subjects.

The term "subject" or "patient" is used interchangeably herein and is intended to mean a mammal including the human species that is treatable by the compound of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In a preferred embodiment, the subject is a human.

The term "synergistically reduction" as used herein means the effect (e.g., reduction in blood glucose level) achieved by use of the combination of the present plant extract of *Hedychium coronarium* Koening and a blood glucose reduction agent, is greater than the sum of the effects that result from using the present plant extract of *Hedychium coronarium* Koening or the blood glucose reduction agent independently. Advantageously, such synergy provides greater efficacy at the same doses.

The term "symptoms related to type II diabetes mellitus" as used herein encompasses acute and/or chronic symptoms that include, at least, high blood sugar, insulin resistance, increased thirst and/or hunger, frequent urination, unexplained weight loss, feeling tired, and sores that do not heal.

The term "excipient" as used herein means any inert substance (such as a powder or liquid) that forms a vehicle/carrier for the active agent. The excipient is generally safe, non-toxic, and in a broad sense, may also include any known substance in the pharmaceutical industry useful for preparing pharmaceutical compositions such as, fillers, diluents, agglutinants, binders, lubricating agents, glidants, stabilizer, colorants, wetting agents, disintegrants, and etc.

II. Treatment of Type II Diabetes Mellitus

The present invention in general, relates to novel finding that the plant extract of *Hedychium coronarium* Koenig, may act synergistically with a known blood glucose reduction agent (such as a DDP-4 inhibitor), in reducing the fasting blood glucose level in a diabetic subject, particularly a type II diabetic subject. Accordingly, the plant extract of *Hedychium coronarium* Koenig, may be used as an add-on medication with any known blood glucose reduction agent for the treatment of type II diabetes mellitus.

In this regard, a particular aspect of the present invention relates to a method of treating a subject suffering from type II diabetes mellitus. The method includes the step of, administering to the subject an effective amount of a plant extract of *Hedychium coronarium* Koenig and a blood glucose reduction agent, in which the combined treatment results in synergistically reduction in the levels of blood glucose in the subject.

The present plant extract of *Hedychium coronarium* Koenig, particularly the ethanol extract obtained from the overground part of *Hedychium coronarium* Koenig, preferably is prepared in accordance with the method described in U.S. patent application Ser. No. 15/359,555 or the method described in U.S. Pat. No. 9,023,407, the disclosure of which is incorporated herein by reference.

Preferably, the present plant extract of *Hedychium coronarium* Koenig is prepared by a method that comprises steps of:

(a) extracting an overground part of *Hedychium coronarium* Koenig with a first solvent to obtain a first extract, wherein the first solvent is (1) petroleum ether, (2) n-hexane, (3) dichloromethane, (4) trichloromethane, (5) ethyl acetate, (6) acetone, or (7) ethanol at a concentration of 70-100% (v/v in water), or (8) a combination of any of (1) to (7), (b) loading the first extract onto a first ion exchange chromatography column, (c) washing the first ion exchange chromatography column with a solution of water and ethanol at a volume ratio from 1:1 to 1:9, and (d) eluting the first ion exchange chromatography column with ethanol at a concentration of at least 70% (v/v in water) to produce the plant extract.

According to preferred embodiments, the overground part of *Hedychium coronarium* Koenig (e.g., pseudostems and/or leaves) is extracted by 95% ethanol (v/v in water).

The thus produced plant extract of *Hedychium coronarium* Koenig may be further subject to at least one chromatography (e.g., high performance liquid chromatography (HPLC)) treatment. According to one preferred embodiments, the plant extract of *Hedychium coronarium* Koenig is subjected to one run of HPLC treatment. According to other preferred embodiments, the plant extract of *Hedychium coronarium* Koenig is subjected to at least two runs of HPLC treatment for further purification. According to one preferred embodiment, the present plant extract of *Hedychium coronarium* Koenig is characterized in having a HPLC spectrum substantially as depicted in FIG. 1A. According to another preferred embodiment, the present plant extract of *Hedychium coronarium* Koenig is characterized in having a HPLC spectrum substantially as depicted in FIG. 1B.

According to preferred embodiments, the plant extract of *Hedychium coronarium* Koenig is administered with one or more blood glucose reduction agent, in which synergistically reduction in blood glucose level of the subject is achieved. Any known blood glucose reduction agent may be used. Preferably, the blood glucose reduction agent is a dipeptidyl peptidase-4 (DPP-4) inhibitor, insulin, an insulin analogue, biguanide, sulfonylurea, thiazolidinedione (TZD), sodium-glucose co-transporter 2 (SGLT2) inhibitor, α-glycosidase inhibitor, a glucagon-like peptide 1 (GLP-1) receptor agonist, or a combination thereof.

DPP-4 inhibitor is gliptins, and suitable examples of gliptins include, but are not limited to, sitagliptin, vildagliptin, saxagliptin, linagliptin, gemigliptin, anagliptin, teneligliptin, alogliptin, trelagliptin, dutogliptin, omarigliptin, berberine, and lupeol. Preferably, the DPP-4 inhibitor is sitagliptin.

The term "insulin" as used herein refers to purified, synthetic and/or biotechnologically derived products that are the same as, or similar to, naturally occurring insulins in structure, use, and intended effect and are of value in the treatment of diabetes mellitus. For example, insulin may be directly recovered from pancreatic tissues of a mammal, such as pancreas glands of farm animals (e.g., pig). Alternatively, insulin may be produced by recombinant technology.

Examples of the insulin analogue include, but are not limited to, glargine, degludec and detemir.

Suitable examples of the biguanide include, but are not limited to, metformin, phenformin, and bufomin.

Suitable examples of sulfonylurea include, but are not limited to, glibenclamide, gliclazide, glimepiride, and glipizide.

Examples of TZD include, but are not limited to, pioglitazone, rosiglitazone, lobeglitazone, ciglitazone, darglitazone, englitazone, netoglitazone, rivoglitazone, and troglitazone.

Examples of SGLT2 inhibitors include, but are not limited to, dapagliflozin, empagliflozin, canagliflozin, Ipragliflozin, tofogliflozin, sergliflozin etabonate, remogliflozin etabonat, and ertugliflozin.

Suitable examples of the α-glycosidase inhibitor include, but are not limited to, acarbose, miglitose, and voglibose.

Suitable examples of the GLP-1 receptor agonist include, but are not limited to, liraglutide, exenatide, albiglutide or LY2189265.

According to some embodiments of the present disclosure, the plant extract of *Hedychium coronarium* Koenig is administered with a DDP-4 inhibitor (e.g., sitagliptin), in which the combined treatment results in synergistically reduction in the levels of blood glucose.

According to other embodiments, the plant extract of *Hedychium coronarium* Koenig is administered to a subject in need thereof along with biguanide (e.g., metformin), in which the combined treatment results in synergistically reduction in the levels of blood glucose.

According to further embodiments of the present disclosure, the plant extract of *Hedychium coronarium* Koenig is administered to a subject in need thereof along with a SGLT2 inhibitor (e.g., empagliflozin), in which the combined treatment results in synergistically reduction in the levels of blood glucose.

According to still further embodiments of the present disclosure, the plant extract of *Hedychium coronarium* Koenig is administered to a subject in need thereof along with biguanide (e.g., metformin) and a DDP-4 inhibitor (e.g., sitagliptin), in which the combined treatment results in synergistically reduction in the levels of blood glucose.

According to embodiments of the present disclosure, the plant extract of *Hedychium coronarium* Koenig and the blood glucose reduction agent may be respectively administered to the subject in need of such treatment in the amount of 0.1 to 100 mg/Kg, such as 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and 100 mg/Kg; preferably, the plant extract of *Hedychium coronarium* Koenig and the blood glucose reduction agent are respectively administered in the amount from about 0.5 to 50 mg/Kg, such as 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 mg/Kg; more preferably, the plant extract of *Hedychium coronarium* Koenig and the blood glucose reduction agent are respectively administered in the amount from about 1 to 20 mg/Kg, such as 1, 2, 3, 4, 5, 6, 7, 8, 9, 10, 11, 12, 13, 14, 15, 16, 17, 18, 19 and 20 mg/Kg. According to certain embodiment of the present disclosure, the plant extract of *Hedychium coronarium* Koenig and the blood glucose reduction agent (i.e., sitagliptin) are respectively administered in the amount of about 6.5 mg/Kg and about 3.5 mg/Kg to a human subject.

According to embodiments of the present disclosure, the plant extract of *Hedychium coronarium* Koenig or the blood glucose reduction agent may be administered independently via any suitable route, which includes, but is not limited to, oral, intraveneous, intramuscular, intraperitoneal, intraarterial, intracranial, and subcutaneous route. In preferred embodiment, an effective amount of the plant extract of *Hedychium coronarium* Koenig and the blood glucose reduction agent are respectively administered orally to the subject in need thereof.

Also encompasses in the present disclosure is a pharmaceutical composition for treating type II diabetes mellitus. The composition comprises the plant extract of *Hedychium coronarium* Koenig, a blood glucose reduction agent; and a pharmaceutically acceptable excipient. Any known blood glucose reduction agent may be used in the present composition. Preferably, the blood glucose reduction agent is a dipeptidyl peptidase-4 (DPP-4) inhibitor, insulin, an insulin analogue, biguanide, sulfonylurea, thiazolidinedione (TZD), sodium-glucose co-transporter 2 (SGLT2) inhibitor, α-glycosidase inhibitor, a glucagon-like peptide 1 (GLP-1) receptor agonist, or a combination thereof.

DPP-4 inhibitor is gliptins, and suitable examples of gliptins include, but are not limited to, sitagliptin, vildagliptin, saxagliptin, linagliptin, gemigliptin, anagliptin, teneligliptin, alogliptin, trelagliptin, dutogliptin, omarigliptin, berberine, and lupeol. Preferably, the DPP-4 inhibitor is sitagliptin.

The term "insulin" as used herein refers to purified, synthetic and/or biotechnologically derived products that are the same as, or similar to, naturally occurring insulins in structure, use, and intended effect and are of value in the treatment of diabetes mellitus. For example, insulin may be directly recovered from pancreatic tissues of a mammal, such as pancreas glands of farm animals (e.g., pig). Alternatively, insulin may be produced by recombinant technology.

Examples of the insulin analogue include, but are not limited to, glargine, degludec and detemir.

Suitable examples of the biguanide include, but are not limited to, metformin, phenformin, and bufomin.

Suitable examples of sulfonylurea include, but are not limited to, glibenclamide, gliclazide, glimepiride, and glipizide.

Examples of TZD include, but are not limited to, pioglitazone, rosiglitazone, lobeglitazone, ciglitazone, darglitazone, englitazone, netoglitazone, rivoglitazone, and troglitazone.

Examples of SGLT2 inhibitors include, but are not limited to, dapagliflozin, empagliflozin, canagliflozin, Ipragliflozin, tofogliflozin, sergliflozin etabonate, remogliflozin etabonat, and ertugliflozin.

Suitable examples of the α-glycosidase inhibitor include, but are not limited to, acarbose, miglitose, and voglibose.

Suitable examples of the GLP-1 receptor agonist include, but are not limited to, liraglutide, exenatide, albiglutide or LY2189265.

To produce the pharmaceutical composition, the plant extract of Hedychium coronarium Koenig is mixed with a blood glucose reduction agent and suitable excipients and formulated into a dosage form suitable for administering orally, intraveneously, intramuscularly, intraperitoneally, intraarterially, intracranially, transmucosally (e.g., inhalation, buccal, and intranasally), or subcutaneously. Suitable excipients are known to those of skill in the art and described, for example, in Handbook of Pharmaceutical Excipients (Kibbe (ed.), $3^{rd}$ Edition (2000), American Pharmaceutical Association, Washington, D.C.), and Remington's Pharmaceutical Sciences (Gennaro (ed.), $20^{th}$ edition (2000), Mack Publishing Inc., Easton, Pa.), which for their disclosure relating to excipients and dosage forms, are incorporated herein by reference. For example, suitable excipients include, but are not limited to, starches, sugars, microcrystalline cellulose, diluents, granulating agents, lubricants, binders, disintegrating agents, wetting agents, lubricants, emulsifiers, coloring agent, release agents, coating agents, sweetening agents, flavoring agents, preservatives, plasticizers, gelling agents, thickeners, hardeners, setting agents, suspending agents, surfactants, humectants, carriers, stabilizers, antioxidants, and combinations thereof.

The pharmaceutical composition are typically provided in dosage forms suitable for administration to a subject by any desired route. One of skill in the art is familiar with various dosage forms that are suitable for use in the present invention. The most suitable route in any given case will depend on the nature and severity of the disease being treated and/or managed. For example, the pharmaceutical compositions may be formulated for administration orally, intraveneously, intramuscularly, intraperitoneally, intraarterially, intracranially, transmucosally (e.g., inhalation, buccal, and intranasally), or subcutaneously. Preferably, the pharmaceutical composition is administered orally. The dosage form of the pharmaceutical composition suitable for oral administration includes, for example, tablets, pills, granules, powders, solutions, suspensions, syrups or capsules. As a method of producing solid dosage form such as a tablet, a pill, granule or powder, it can be formed by conventional techniques using a pharmaceutically acceptable carrier such as excipient, binder, or disintegrant and etc. The solid dosage form for oral administration may optionally be scored or prepared with coating and shells, such as entering coatings, and coatings for modifying the rate of release. Further, any of the solid dosage form may be encapsulated in soft and hard gelatin capsules using any of the excipients known in the art.

The plant extract of Hedychium coronarium Koenig and the blood glucose reduction agent may also be formulated into a liquid dosage form for oral administration. Suitable formulation include emulsion, solutions, suspension or syrup, it can be produced by conventional techniques using diluents commonly used in the art, such as water, glycerol esters, alcohols, vegetable oils, and etc. The liquid formulation may optionally include adjuvants such as wetting agents, emulsifying agents, and suspending agents, sweetening, flavoring, coloring, and preservative agents. The liquid formulation may also be filled into soft gelatin capsules. For example, the liquid may include a solution, suspension, emulsion, precipitate, or any other desired liquid media carrying the plant extract of Hedychium coronarium Koenig and the blood glucose reduction agent. The liquid may be designed to improve the solubility of the plant extract of Hedychium coronarium Koenig and the blood glucose reduction agent upon release, or may be designed to form a drug-containing emulsion or dispersed phase upon release. Examples of such techniques are well known in the related art. Soft gelatin capsules may be coated, as desired, with a functional coating, such as to delay the release of the drug.

In the case of parenteral administration, the plant extract of Hedychium coronarium Koenig and the blood glucose reduction agent may be formulated into injectable forms for intravenous, subcutaneous or intramuscular administration. An injection can be prepared by dissolving the plant extract of Hedychium coronarium Koenig and the blood glucose reduction agent in water soluble solution such as physiological saline, or water insoluble solution consisting of organic esters such as propylene glycol, polyethylene glycol, or vegetable oils (e.g., sesame oil).

In the case of transdermal administration, for example, a dosage form as an ointment or a cream can be employed. The ointment can be produced by mixing the plant extract of Hedychium coronarium Koenig and the blood glucose reduction agent with fats or oils and etc; and the cream can be produced by mixing the plant extract of Hedychium coronarium Koenig and the blood glucose reduction agent with emulsifiers. The transdermal formulation may be in a form of a liquid or a powdery formulation. In a liquid formulation, water, salt solution, phosphate buffer, acetate buffer and etc may be used as a base; it may also contain surfactants, antioxidants, stabilizers, preservatives or tackifiers. In a powdery formulation, it may contain water-absorbing materials such as water-soluble polyacrylates, cellulose low-alkyl esters, polyethylene glycol polyvinyl pyrrolidone, amylase and etc, and non-water absorbing materials such as cellulose, starches, gums, vegetable oils or cross-linked polymers. Further, antioxidants, colorants, preservatives may be added to the powdery formulation. The liquid or powdery formulation may be administered by use of a spray apparatus.

In the case of rectal administration, it may be in the form of suppository using a gelatin soft capsule.

In case of inhalation through nose or mouth, a solution or suspension containing the plant extract of *Hedychium coronarium* Koenig and the blood glucose reduction agent and a pharmaceutical excipient generally accepted for this purpose is inhaled through an inhalant aerosol spray. Alternatively, the plant extract of *Hedychium coronarium* Koenig and the blood glucose reduction agent in the form of a powder may be administered through inhalator that allows direct contact of the powder with the lung. To these formulations, if necessary, pharmaceutical acceptable carriers such as isotonic agents, preservatives, dispersions, or stabilizers may be added. Further, if necessary, these formulations may be sterilized by filtration, or by treatment with heat or irradiation.

In general, the pharmaceutical composition comprising the plant extract of *Hedychium coronarium* Koenig and the blood glucose reduction agent is administered to the subject in single or divided doses 2, 3, 4, 5, 6 or more times each day. Alternatively, the dose may be delivered once every 2, 3, 4, 5, 6 or more days. In one preferred embodiment, the pharmaceutical composition is administered once per day. In another embodiment, the pharmaceutical composition is administered twice per day.

A further aspect of the present invention relates to a kit for the treatment of type II diabetes mellitus. The kit includes, at least, a first container containing the present plant extract of *Hedychium coronarium* Koenig; and a second container containing therein a blood glucose reduction agent; and a legend providing instruction to the user on how to administer the plant extract of *Hedychium coronarium* Koenig and the blood glucose reduction agent for the treatment of type II diabetes.

According to preferred embodiments of the present disclosure, the kit includes two containers, in which the first container housed therein a dosage form of the plant extract of *Hedychium coronarium* Koenig, while the second container housed therein a dosage form of any of a DDP-4 inhibitor (e.g., sitagliptin), a biguanide, a SGLT2 inhibitor, or a combination thereof; and a legend providing instructions to a user on how to use the kit. The legend may be in the form of a pamphlet, tape, CD, VCD or DVD.

The present plant extract of *Hedychium coronarium* Koenig and the blood glucose reduction agent in the present kit may be independently provided in dosage forms suitable for administration to a subject by any desired route. One of skill in the art is familiar with various dosage forms that are suitable for use in the present invention. The most suitable route in any given case will depend on the nature and severity of the disease being treated and/or managed. For example, the present plant extract of *Hedychium coronarium* Koenig and the blood glucose reduction agent may be formulated for administration orally, intraveneously, intramuscularly, intraperitoneally, intraarterially, intracranially, transmucosally (e.g., inhalation, buccal, and intranasally), or subcutaneously. Preferably, the present plant extract of *Hedychium coronarium* Koenig and the blood glucose reduction agent are respectively administered orally.

The present invention will now be described in further detail with reference to the following examples. However, it should be understood that the present invention is not limited to the specified examples.

EXAMPLES

Materials and Methods

Animals.

Non-insulin dependent diabetic mellitus (NIDDM) male db/db (BKS.Cg-Dock $7^m$+/+Lepr$^{db}$/JNarl) were used in the present study. They were supplied by National Laboratory Animal Center (NLAC) (Taipei, Taiwan). They exhibited hyperinsulinemia, hyperglycemia, and islet atrophy and were used at about 11-13 weeks of age.

All were maintained in the animal facility with controlled temperature (20-24° C.), humidity (50-80%) and a 12 h/12 h light/dark cycle (light on at 7:00 a.m.) with food and water provided ad libitum. Experimental procedures for handling the mice complied with relevant regulations set forth in "Guide for the Care and Use of Laboratory Animals: Eighth Edition" (National Academies Press, Washington, D.C., 2011) in AAALAC-accredited laboratory animal facility. (Eurofins Panlabs Taiwan, Ltd.)

NIDDM Mice and Treatment

NIDDM mice were acclimated for at least 5 days and then grouped for treatment when the average blood glucose value was ≥180 mg/dl after overnight fasting (day 0). Test compounds (i.e., HC extract (40 mg/Kg from day 1 to day 14; 80 mg/Kg from day 14 to day 28, p.o.), sitagliptin (40 mg/Kg, p.o.), or the combination of HC extract and sitagliptin) at the designated dose was fed to each mice by oral gavage from day 1, and continued for 27 consecutive days to day 28.

Blood glucose, insulin, glucagon, glycated haemoglobin (HbA1c) levels were measured on designated days after overnight fasting. Then, oral glucose tolerance test (OGTT) was performed to evaluate effects of respective treatments on glucose homeostasis. Body weight of each test animal was also measured during the study period.

Oral Glucose Tolerance Test (OGTT)

The db/db mice were randomly divided into 4 groups: (1) the vehicle control group, (2) the HC extract (80 mg/kg), (3) the sitagliptin (40 mg/Kg) group, and (5) the HC extract (80 mg/kg)+sitagliptin (40 mg/Kg) group.

The mice were fasted for 7 hours and then respectively received the indicated treatments. After 30 minutes, each mice was administered with glucose at a total amount of 5 g/kg, orally (2.5 g/kg) and subcutaneously (2.5 g/kg). Blood was drawn from each mice at the intervals of 0, 30, 60, 90 and 120 minutes for the measurement of glucose (mg/DL).

Statistics

Results were expressed as the mean±standard error of the mean (SEM). Unpaired student's t-test or 1-way ANOVA was used for statistical comparisons between substance-treated and vehicle-treated groups. Differences are considered significant at $P<0.05$, vs vehicle control.

Example 1 Preparation of the HC Extract in general, the extract of the overground part of *Hedychium coronarium* Koenig (hereinafter "HC extract") was prepared in accordance with procedures described in U.S. Pat. No. 9,023,407, the disclosure of which is incorporated herein by reference.

1.1 Preparation of the Ethanol Extract of *Hedychium coronarium* Koenig

Dried leaves and pesudostems of *Hedychium coronarium* were extracted with 95% ethanol twice in a weight to volume ratio of 1:15. The 95% EtOH extracts were concentrated and passed through a diaion column, which was eluted sequentially with $H_2O$ and 95% EtOH (2:8) (F1), 95% EtOH (F2) and 95% EtOH and EtOAc (1:1) (F3). The F2 fraction (or the "HC extract") was collected and used in subsequent glucose tolerance experiments.

The F2 fraction exhibited a characteristic high performance liquid chromatography (HPLC) spectrum as depicted in FIG. 1A, in which the HPLC was conducted under the following conditions: mobile phase at 0 minute: 66% MeOH/34% $H_2O$; at 60 minute: 100% MeOH/0% $H_2O$; at 76 minute: 100% MeOH/0% $H_2O$; at 78 minutes: 66% MeOH/34% $H_2O$; and at 86 minutes: 66% MeOH/34% $H_2O$; flow rate: 1.0 mL/min; and detection wavelength: 254 nm.

1.2 Preparation of the Water Extract of *Hedychium coronarium* Koenig

Dried leaves and pesudostems of *Hedychium coronarium* was extracted with 50% ethanol twice in a weight to volume ratio of 1:15. (w:v=1:15). The 50% ethanol extracts were concentrated and pass through a diaion column, which was eluted sequentially with $H_2O$ and 30% ethanol to produce the HC extract.

The thus produced HC extract was subjected to HPLC analysis using a linear gradient of acetonitrile (ACN) and water containing 0.1% trifluoroacetic acid (TFA), and was found to exhibit a characteristic spectrum as depicted in FIG. 1B, in which the HPLC analysis was conducted under the following conditions: mobile phase at 0 minute: 10% ACN (in 0.05% TFA)/90% $H_2O$ (in 0.05% TFA); at 80 minute: 17% ACN (in 0.05% TFA)/83% $H_2O$ (in 0.05% TFA); at 90 minute: 100% ACN (in 0.05% TFA)/0% $H_2O$ (in 0.05% TFA); at 100 minute: 100% ACN (in 0.05% TFA)/0% $H_2O$ (in 0.05% TFA); at 102 minute: 10% ACN (in 0.05% TFA)/90% $H_2O$ (in 0.05% TFA); and at 110 minute: 10% ACN (in 0.05% TFA)/90% $H_2O$ (in 0.05% TFA); flow rate: 1.0 mL/min; and detection wavelength: 254 nm.

Example 2 the Combined Treatment of HC Extract and DDP-4 Inhibitor on Blood Glucose Level and Glucose Tolerance in Diabetic Mice In this example, the effects of the HC extract of Example 1 and/or sitagliptin (i.e., DDP-4 inhibitor) on blood glucose level and glucose tolerance were evaluated by use of NIDDM mice, which were born with mild defects in the insulin signaling cascade that gave rise to insulin resistance and subsequent progression to a diabetic phenotype. The animals were treated by the manner described in the "Material and Methods" section.

Figure 2:
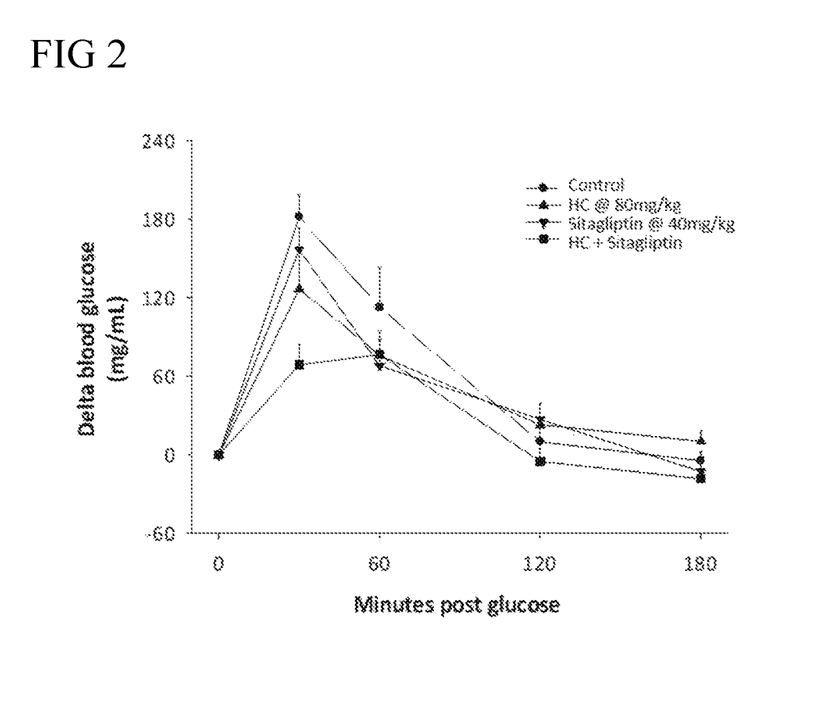
FIG. 2 is a line graph illustrating the effects of HC extract and/or sitagliptin on the level of blood glucose in NIDDM mice in accordance with Example 2 of this invention.

As expected, the HC extract (80 mg/Kg) and sitagliptin (40 mg/Kg) could independently result in a reduction in the fasting blood glucose level in NIDDM mice; however, what was more surprised was, when the HC extract and sitagliptin were administered together, a synergistic reduction in the fasting blood glucose level was found 30 minutes post glucose treatment, as compared with that of the HC extract alone or sitagliptin alone treated NIDDM mice (FIG. 2).

Figure 3:
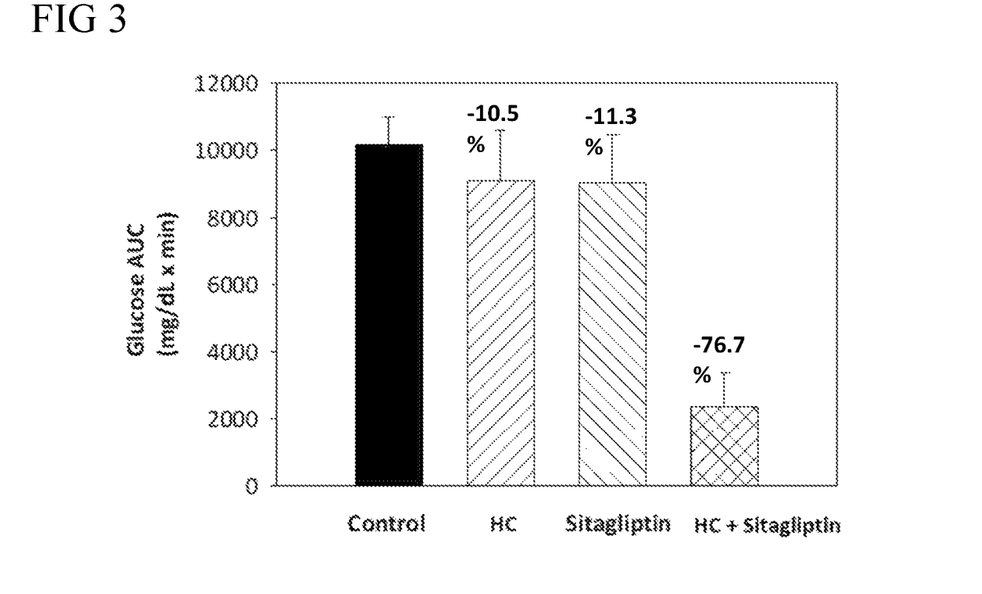
FIG. 3 is a bar graph depicting the cumulated blood glucose levels taken from the 30-minutes time point post-glucose treatment of FIG. 2, in which "a" denotes HC extract+sitagliptin treated vs. control, p=0.005, "b" denotes HC extract+sitagliptin treated vs. HC extract, p=0.006, and "c" denotes HC extract+sitagliptin treated vs. sitagliptin, p=0.006, after one-way ANOVA analysis.

The data at 30 minutes time point post glucose treatment was further analyzed and presented in FIG. 3. The HC extract (80 mg/Kg) alone resulted in about 10.5% reduction in the level of total blood glucose, sitagliptin (40 mg/Kg) was slightly more potent that the HC extract, in which about 11.3% reduction in the level of total blood glucose was observed. Surprisingly, when the HC extract and sitagliptin were administered together, a total of 76.7% reduction in the level of total blood glucose was found.

Example 3 Combined Treatment of HC Extract and DDP-4 Inhibitor, Biguanide, and/or SGLT2 Inhibitor on Blood Glucose Level and Glycated Haemoglobin (HbA1c) Level in NIDDM Mice Based on the finding of example 1, the combined effects of the HC extract and at least one blood glucose reduction agent listed bellowed on fasting blood glucose and glycated haemoglobin (HbA1c) will be further investigated in NIDDM mice. The blood glucose reduction agent is any of metformin (150 mg/Kg), sitagliptin (40 mg/Kg), empagliflozin (10 mg/Kg), or a combination thereof. Accordingly, the test subjects will be randomly divided into 10 groups (n=7 in each group), and receive treatments of (1) control, (2) the HC extract (80 mg/Kg), (3) the HC extract (80 mg/Kg)+sitagliptin (40 mg/Kg), (4) the HC extract (80 mg/Kg)+empagliflozin (10 mg/Kg), (5) the HC extract (80 mg/Kg)+metformin (150 mg/Kg), (6) sitagliptin (40 mg/Kg)+metformin (150 mg/Kg), (7) empagliflozin (10 mg/Kg) metformin (150 mg/Kg), (8) the HC extract (80 mg/Kg)+sitagliptin (40 mg/Kg)+metformin (150 mg/Kg), (9) the HC extract (80 mg/Kg)+empagliflozin (10 mg/Kg) metformin (150 mg/Kg), and (10) sitagliptin (40 mg/Kg)+ empagliflozin (10 mg/Kg) metformin (150 mg/Kg), will be further evaluated in NIDDM mice.

It is expected that the HC extract would synergistically reduce the blood glucose level when it is administered with either metformin, sitagliptin, empagliflozin, or a combination thereof; as well as in the level of long-term diabetic indicator—HbA1c.

Taken together of the findings in the working examples, the combined treatment of sitagliptin and the HC extract produces synergistic reduction in blood glucose level. Accordingly, the HC extract is suitable for use as an add-on medicament for the current treatment of type II diabetes mellitus, such as biguanide, DPP-4 inhibitor, and the SGLT2 inhibitor.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for treating a subject having type II diabetes comprising administering to the subject an effective amount of a plant extract of *Hedychium coronarium* Koenig and dipeptidyl peptidase-4 (DPP-4) inhibitor, so that a synergistically reduction in the blood glucose level in the subject is achieved, wherein the plant extract of *Hedychium coronarium* Koenig and the DPP-4 inhibitor are respectively administered to the subject in the amount of 5.5-11 mg/kg and 1.7-3.5 mg/Kg.

2. The method of claim 1, wherein the DPP-4 inhibitor is selected from the group consisting of sitagliptin, vildagliptin, saxagliptin, linagliptin, gemigliptin, anagliptin, teneligliptin, alogliptin, trelagliptin, dutogliptin, omarigliptin, berberine, and lupeol.

3. The method of claim 2, wherein the DPP-4 inhibitor is sitagliptin.

4. The method of claim 2, further comprising administering to the subject a biguanide in the amount of 12-16.7 mg/Kg, wherein the biguanide is metformin, phenformin, or buformin.

5. The method of claim 4, wherein the biguanide is metformin.

6. The method of claim 5, wherein the blood glucose reduction agent is a combination of sitagliptin and metformin.

7. The method of claim 1, wherein the plant extract of *Hedychium coronarium* Koenig is produced by a method comprising:
   (a) extracting an overground part of *Hedychium coronarium* Koenig with a first solvent to obtain a first extract, wherein the first solvent is (1) petroleum ether, (2) n-hexane, (3) dichloromethane, (4) trichloromethane, (5) ethyl acetate, (6) acetone, or (7) ethanol at a concentration of 70-100% (v/v in water), or (8) a combination of any of (1) to (7),
   (b) loading the first extract onto a first ion exchange chromatography column,
   (c) washing the first ion exchange chromatography column with a solution of water and ethanol at a volume ratio from 1:1 to 1:9, and
   (d) eluting the first ion exchange chromatography column with ethanol at a concentration of at least 70% (v/v in water) to produce the plant extract *Hedychium coronarium* Koenig.

8. The method of claim 7, wherein the plant extract of *Hedychium coronarium* Koenig is characterized in having a high performance liquid chromatography (HPLC) spectrum substantially as depicted in FIG. 1A or 1B.

9. The method of claim 1, wherein the plant extract of *Hedychium coronarium* Koenig and the DPP-4 inhibitor are respectively administered in the amount of 11 mg/Kg and 1.67 mg/Kg.

10. The method of claim 1, wherein the plant extract of *Hedychium coronarium* Koenig and the DPP-4 inhibitor are respectively administered in the amount of 6.5 mg/Kg and 3.5 mg/Kg.

\* \* \* \* \*